United States Patent
Brady et al.

[11] Patent Number: 5,810,833
[45] Date of Patent: *Sep. 22, 1998

[54] DEFORMABLE LENS INSERTION APPARATUS

[75] Inventors: Daniel G. Brady, Mission Viejo; Edward R. Zaleski, Santa Ana; Anthony V. Lemus, Tustin, all of Calif.

[73] Assignee: Allergan, Waco, Tex.

[ * ] Notice: The term of this patent shall not extend beyond the expiration date of Pat. No. 5,562,676.

[21] Appl. No.: 681,563

[22] Filed: Jul. 29, 1996

Related U.S. Application Data

[62] Division of Ser. No. 382,948, Feb. 1, 1995, Pat. No. 5,562,676, which is a continuation of Ser. No. 154,240, Nov. 18, 1993, abandoned.

[51] Int. Cl.$^6$ ................................................ A61F 11/00
[52] U.S. Cl. .................................... 606/107; 623/6
[58] Field of Search ........................ 606/107, 161, 606/162; 623/5, 6

[56] References Cited

U.S. PATENT DOCUMENTS

| | | |
|---|---|---|
| 450,266 | 4/1891 | Truax . |
| 2,450,138 | 9/1948 | Harwood . |
| 3,678,927 | 7/1972 | Soichet . |
| 3,703,174 | 11/1972 | Smith . |
| 4,026,281 | 5/1977 | Mayberry et al. . |
| 4,122,556 | 10/1978 | Poler . |
| 4,190,049 | 2/1980 | Hager et al. . |
| 4,198,980 | 4/1980 | Clark . |
| 4,214,585 | 7/1980 | Bailey, Jr. . |
| 4,244,370 | 1/1981 | Furlow et al. . |
| 4,249,271 | 2/1981 | Poler . |
| 4,251,887 | 2/1981 | Anis . |
| 4,253,199 | 3/1981 | Banko . |
| 4,257,521 | 3/1981 | Poler . |
| 4,298,994 | 11/1981 | Clayman . |
| 4,303,268 | 12/1981 | Davidson . |
| 4,325,875 | 4/1982 | Nevyas . |
| 4,349,027 | 9/1982 | DiFfrancesio . |
| 4,373,218 | 2/1983 | Schachar . |
| 4,423,809 | 1/1984 | Mazzocco . |
| 4,446,581 | 5/1984 | Blake . |
| 4,449,257 | 5/1984 | Koeniger . |
| 4,462,404 | 7/1984 | Schwarz et al. . |

(List continued on next page.)

FOREIGN PATENT DOCUMENTS

| | | |
|---|---|---|
| 2191439 | 12/1987 | United Kingdom . |
| 8201646 | 5/1982 | WIPO . |
| 8808288 | 11/1988 | WIPO . |

OTHER PUBLICATIONS

Microsert II™, Model IM 002, Directions for use with the Chiroflex™II, Chiron IntraOptics, Jul. 1993.
Folding & Inserting Silicone Intraocular Lens Implants, Faulkner, Nov. 1987.
IOL & Ocular Surgery News, vol. 1, No. 14 (Jul. 1983).
Cataract Refract Surg., vol. 15, Mar. 1989, Christ et al Evaluation of the chemical, optical, and mechanical properties of elastomeric Intraocular lens materials and their clinical significance.

*Primary Examiner*—Kien T. Nguyen
*Assistant Examiner*—Justine R. Yu
*Attorney, Agent, or Firm*—Frank J. Uxa

[57] ABSTRACT

Apparatus for insertion of intraocular lenses into the eye are disclosed. In one embodiment, the apparatus comprises a loading chamber and an injection portion. The loading chamber has a proximal end and a distally extending opening. The loading chamber defines a first lumen and is adapted to receive an intraocular lens in an unfolded state at the distally extending opening and to fold the intraocular lens and maintain the intraocular lens folded as the intraocular lens is placed in the first lumen. The injection portion defines a second lumen aligned with the first lumen and is adapted to receive the folded intraocular lens from the first lumen in the second lumen. The injection portion has an open distal end through which the folded intraocular lens from the second lumen passes to be inserted into an eye.

21 Claims, 2 Drawing Sheets

U.S. PATENT DOCUMENTS

| | | |
|---|---|---|
| 4,463,457 | 8/1984 | Kelman . |
| 4,468,820 | 9/1984 | Uhler et al. . |
| 4,490,860 | 1/1985 | Rainin . |
| 4,527,294 | 7/1985 | Heslin . |
| 4,573,998 | 3/1986 | Mazzocco . |
| 4,588,405 | 5/1986 | Knolle, Jr. ................................. 623/6 |
| 4,600,004 | 7/1986 | Lopez et al. . |
| 4,619,657 | 10/1986 | Keates et al. . |
| 4,681,102 | 7/1987 | Bartell . |
| 4,702,244 | 10/1987 | Mazzocco . |
| 4,715,373 | 12/1987 | Mazzocco et al. . |
| 4,732,150 | 3/1988 | Keener, Jr. . |
| 4,747,404 | 5/1988 | Jampel et al. . |
| 4,759,359 | 7/1988 | Willis et al. . |
| 4,763,650 | 8/1988 | Hauser . |
| 4,765,329 | 8/1988 | Cumming et al. ...................... 606/107 |
| 4,769,034 | 9/1988 | Poley . |
| 4,781,719 | 11/1988 | Kelman . |
| 4,785,810 | 11/1988 | Baccala et al. . |
| 4,791,924 | 12/1988 | Kelman . |
| 4,813,957 | 3/1989 | McDonald . |
| 4,819,631 | 4/1989 | Poley . |
| 4,834,094 | 5/1989 | Patton et al. ............................ 606/107 |
| 4,836,201 | 6/1989 | Patton et al. . |
| 4,844,065 | 7/1989 | Faulkner . |
| 4,844,093 | 7/1989 | Jampel et al. . |
| 4,880,000 | 11/1989 | Holmes et al. . |
| 4,917,680 | 4/1990 | Poley . |
| 4,919,130 | 4/1990 | Stoy et al. . |
| 4,934,363 | 6/1990 | Smith et al. . |
| 4,976,716 | 12/1990 | Cumming . |
| 4,988,352 | 1/1991 | Poley . |
| 5,007,913 | 4/1991 | Dulebohn et al. ......................... 623/6 |
| 5,098,439 | 3/1992 | Hill et al. . |
| 5,123,905 | 6/1992 | Kelman . |
| 5,190,552 | 3/1993 | Kelman . |
| 5,260,021 | 11/1993 | Zeleznick . |
| 5,275,604 | 1/1994 | Rheinish et al. ........................ 606/107 |
| 5,474,562 | 12/1995 | Orchowski et al. ....................... 623/6 |
| 5,562,676 | 10/1996 | Brady et al. ............................ 606/107 |
| 5,616,148 | 4/1997 | Eagles et al. ........................... 606/107 |

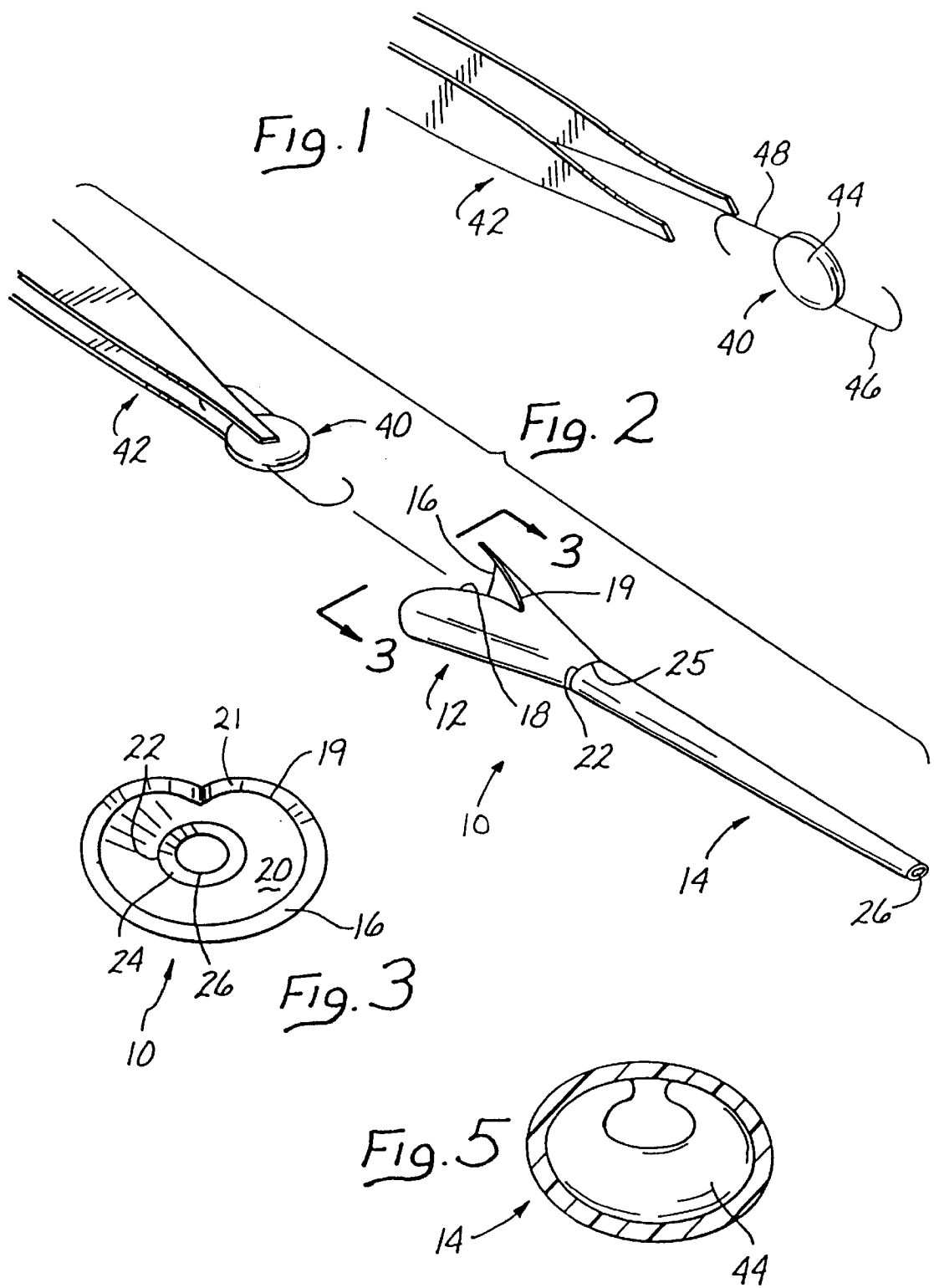

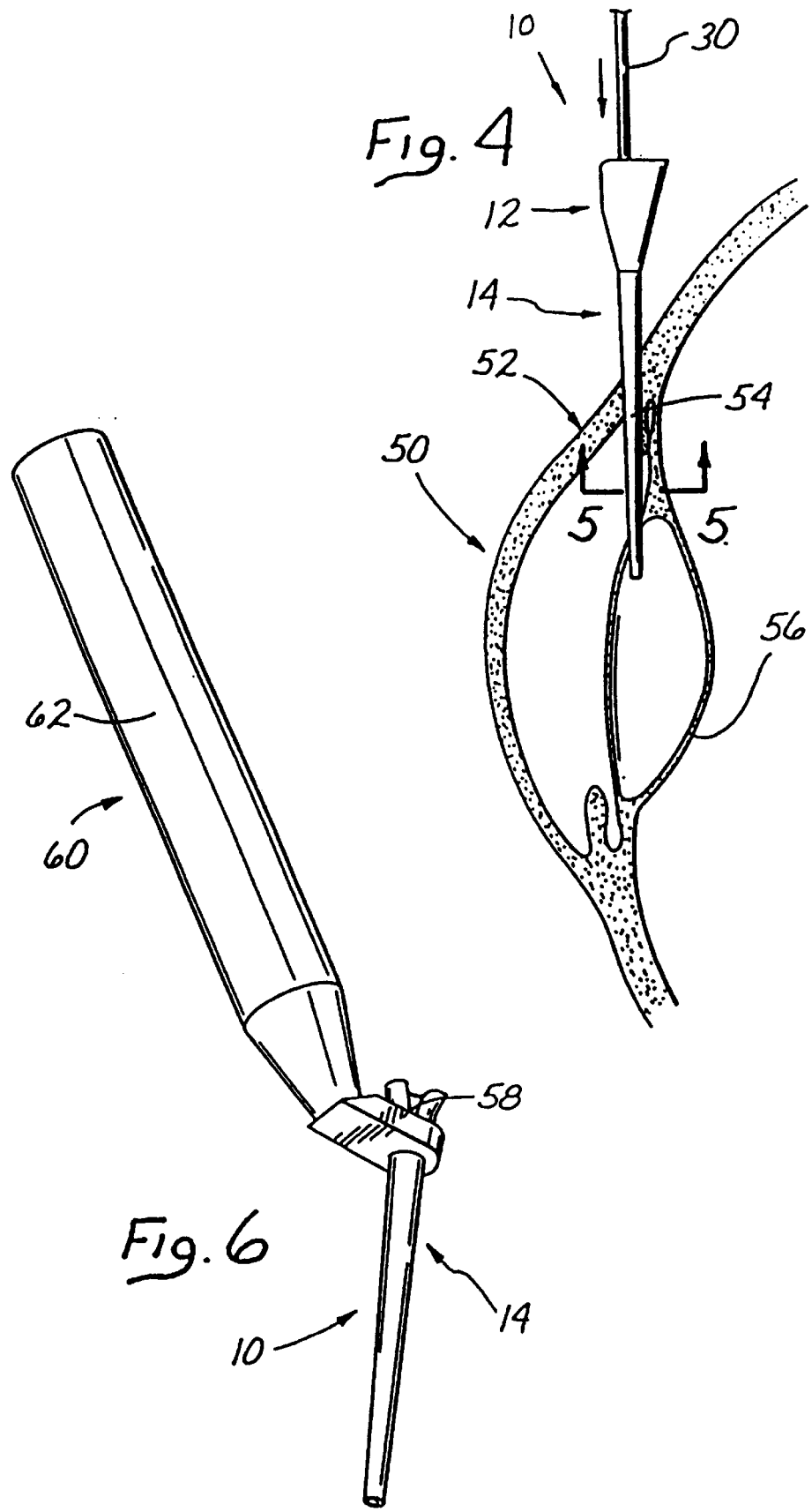

DEFORMABLE LENS INSERTION APPARATUS

This is a division of application Ser. No. 08/382,948 filed Feb. 1, 1995, now U.S. Pat. No. 5,562,676, which, in turn, is a continuation of Ser. No. 08/154,240 now abandoned, filed Nov. 18, 1993.

BACKGROUND OF THE INVENTION

The present invention relates to an apparatus for inserting a deformable or foldable lens into an eye. More particularly, the invention relates to such an apparatus constructed so as to fold the intraocular lens and to be proximally loaded with the intraocular lens to be inserted.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic that extends from the optic and becomes affixed in the eye to secure the lens in position. The optic normally includes an optically clear lens. Implantation of such IOLs into the eye involves making an incision in the eye. It is advantageous, to reduce trauma and speed healing, to have the incision sized as small as possible.

IOLs are known which are foldable (deformable) so that the IOL can be inserted through a smaller incision into the eye. A substantial number of instruments have been proposed to aid in inserting such a foldable lens in the eye. Many of these instruments involve pre-folding the lens before the lens is placed in the insertion device. While this hand folding allows the lens to be inserted through a relatively small incision, it is time consuming and the added handling can damage the lens.

Many of the prior art IOL insertion systems load and/or fold the IOL at the distal end, that is at the end closest to the eye or the end inserted into the eye. Such "distal loading" systems often disadvantageously include a space consuming loading component at or near the distal end of the system which causes the distal end to be relatively large. This relatively large distal end makes inserting the IOL through a small incision more difficult, if not impossible. Also, the IOL itself may structurally compromise the distal end of the inserter as a result of the distal end loading operation. Systems which fold and load the IOL proximally of the distal end provide certain advantages, such as reduced stress on the IOL and/or inserter, relative to "distal loading" systems.

Mazzocco U.S. Pat. No. 4,573,998 discloses a number of IOL insertion devices. One of these, in which the IOL is loaded proximally, provides that the unfolded IOL is maintained in a suitable liquid medium in a chamber integral with the insertion tube. Fluid pressure is used to cause the unfolded IOL to pass from the chamber into the insertion tube or cannula and then into the eye. Using fluid pressure to move the IOL from the chamber through the cannula into the eye can result in exposing the eye to relatively high fluid pressures which can damage the eye. The construction of this device, particularly proximally of the chamber, makes folding the IOL in the chamber by mechanical means, such as by using forceps, very difficult, if not impossible.

SUMMARY OF THE INVENTION

New apparatus and methods useful for surgically inserting a foldable IOL into an eye have been discovered. The present invention allows the use of a relatively small incision in the eye for IOL insertion purposes. In addition, the present apparatus can be proximally loaded with the IOL at the time of the surgery. This allows the surgeon to inspect the IOL, in its unfolded state, immediately before insertion. Further, this proximal loading of the IOL is done with a reduced amount of stress on the lens. Thus, the IOL has a reduced chance or probability of being damaged during the loading process. Moreover, the loading process is performed very speedily and reliably. The present apparatus are straightforward in construction and can be produced and used in a number of forms to suit the individual needs of the surgical application involved and/or the likes and dislikes of the surgeon. Using the present apparatus, the surgeon can easily and controllably place an IOL into a patient's eye.

In one broad aspect of the present invention, apparatus for insertion of an IOL into a small incision of an eye are provided and comprise a loading chamber and an injection cone. In one embodiment, the loading chamber has a proximal end and a distally extending opening, preferably a distally extending proximal end opening. The loading chamber defines a first lumen and is adapted to receive an IOL, preferably in an unfolded state, at the distally extending opening and to fold the IOL and maintain the IOL folded as the IOL is placed in the first lumen. In another embodiment, the loading chamber defines a first lumen and includes an open proximal end defining a non-circular proximal opening in communication with the first lumen. The loading chamber is adapted to receive an IOL, preferably in an unfolded state, at the open proximal end and to fold the IOL and maintain the IOL folded as the IOL is passed into and through the first lumen. The injection portion defines a second lumen aligned, preferably contiguous, with the first lumen. The injection portion is adapted to receive the folded IOL from the first lumen in the second lumen. The injection portion has an open distal end through which the folded IOL from the second lumen passes to be inserted into an eye.

The inclusion of a distally extending opening or a non-circular proximal opening in the loading chamber provides important advantages. The distally extending opening or the non-circular proximal opening acts to facilitate the folding of the IOL as the IOL is placed in the first lumen. The loading chamber can thus be considered to be foldable about the IOL in that the distally extending opening or the non-circular proximal opening of the loading chamber is sized and configured to facilitate the folding of the IOL passing through the distally extending opening or the non-circular proximal opening into the first lumen defined by the loading chamber.

In a further embodiment of the present invention, the loading chamber has an open proximal end and defines a first lumen, and the injection portion is as described previously. The open proximal end of the loading chamber is the proximal terminus of the first lumen. The loading chamber is adapted to receive an IOL, preferably in an unfolded state, at the open proximal end and to fold the IOL and maintain the IOL folded as the IOL is passed into and through the first lumen. In this embodiment, the loading chamber and the injection portion are a unitary or integral structure which structure proximally terminates at the open proximal end of the loading chamber. This structure is designed to facilitate the use of mechanical means, such as a forceps and the like, to insert the IOL into and through the open proximal end of the loading chamber. In so doing, the IOL is folded and is maintained folded in the first lumen of the loading chamber. The use of a forceps and the like to fold the IOL in the first lumen has substantial advantages, for example, enhanced safety, relative to the system employed by the above-noted Mazzocco patent which uses fluid pressure to pass the unfolded IOL into a tube for folding.

The present systems are preferably packaged in sterile condition. Also, since the injection portion may be inserted into the eye, it is preferred that the injection portion be made of a material which is biocompatible. Further, it is preferred that the distal end of the injection portion be sized to pass into a 3.2 mm or smaller incision in an eye.

The diameter of at least one of the first lumen and the second lumen, preferably both of such lumens, gradually decreases in the distal direction along its length. This preferred tapering facilitates folding of the IOL and/or maintaining the IOL folded as it passes through the first lumen and the second lumen.

The present invention further includes methods for inserting an IOL into an eye, preferably through a small incision into an eye. Such methods comprise placing an IOL in a insertion apparatus, as described above; placing the distal end of the injection portion of the insertion apparatus in proximity to an eye or into an eye; and causing the folded IOL to pass out of the distal end opening of the injection portion and into the eye. This causing may comprise pushing or pulling, preferably pushing, the IOL out of the distal end opening of the injection portion. If the injection portion is placed into the eye, after the IOL is passed into the eye the injection portion is withdrawn from the eye. The IOL in its unfolded state remains in the eye. The present methods can be performed, with various modifications, using the various embodiments of the insertion apparatus set forth herein. An incision is made in the eye prior to inserting the IOL into the eye. Once the IOL has been inserted into the eye, the incision can be mended.

The foldable IOLs insertable in the eye using the present apparatus and methods may be of any configuration suitable to perform the desired function in the eye. Such lenses often include a lens body or optic which has optical properties in the eye. Such lens body is foldable as set forth herein. In many instances the lens body,is generally circular. However, other configurations are also useful. In addition, the IOLs may, and preferably do, include at least one flexible fixation member which is secured or attached to the optic. This flexible fixation member acts to fix the IOL in position in the eye. Examples of flexible fixation members include flexible haptics which are preferably radially resilient and extend outwardly from the periphery of the lens body. Specific examples of such flexible haptics include those commonly known as J-loops and C-loops. Such haptics engage appropriate circumferential eye tissue adjacent the iris or within the capsular bag to fix the lens in position in the eye. A very useful IOL includes a plurality of, especially two, such flexible haptics.

The lens body may be made of any suitable material such as polymethamethacrylate, silicone, hydrogel or other well known materials for foldable IOL instruction. Preferably the optic also includes an ultraviolet light absorber. The flexible fixation member or members may be made of any suitable material such as polymethamethacrylate, prolene, polypropylene, nylon, silicone or other materials suitable for implantation into the eye.

As used herein, the terms "foldable" and "deformable" mean that an IOL, and in particular the lens body or optic of an IOL, can be temporarily reshaped so as to pass through a smaller incision relative to the incision required if the IOL was not temporarily reshaped.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a perspective view illustrating the positioning of a forceps and an IOL to be inserted using an apparatus in accordance with the present invention.

FIG. 2 is a perspective view showing the IOL in the grasp of the forceps being inserted through the distal end opening of one embodiment of the present IOL insertion apparatus.

FIG. 3 is a cross-sectional view taken along line 3—3 of FIG. 2.

FIG. 4 is a schematic illustration showing the IOL insertion apparatus shown in FIG. 3 being used to insert an IOL in the eye.

FIG. 5 is a cross-sectional view taken along line 5—5 of FIG. 4.

FIG. 6 is a perspective view showing the embodiment of the present IOL insertion apparatus shown in FIG. 2 coupled to a hand tool for use.

DETAILED DESCRIPTION OF THE INVENTION AND DRAWINGS

FIGS. 2, 3, 4 and 5 show, in general, an IOL insertion apparatus 10 which includes a loading chamber 12 and an injection portion 14.

Loading chamber 12 includes a proximal end 16, a distally extending proximal end opening 18 and a first lumen 20. This first lumen 20 extends from the distally extending proximal end opening 18 to the distal end 22 of loading chamber 12 and is contiguous with second lumen 24 defined by injection portion 14. The cross-sections of loading chamber 12 and of first lumen 20 decrease from the proximal end 16 to the distal end 22 of the loading chamber. The distally extending proximal end opening 18, which is non-circular, is defined by a generally V-shaped through notch 19 which is formed in the sidewall 21 of loading chamber 12.

Injection portion 14 defines a second lumen 24 and includes a distal end opening 26 which is generally elliptical in cross-section, although other configurations, such as a circular cross-section, may be employed. The cross-sections of injection portion 14 and second lumen 24 decrease gradually from the proximal end 25 to the distal end opening 26 of the injection portion.

IOL insertion apparatus 10 is made, for example, molded, as a single or unitary structure which terminates proximally at the proximal end 16 of loading chamber 12. Although the apparatus 10 can be made of any suitable material of construction, a preferred material is a transparent polymeric material, such as polypropylene. The use of a transparent material is advantageous in that the exact location in apparatus 10 of the IOL to be inserted is more readily ascertained by looking through apparatus 10. In addition, the apparatus 10 is made of a biocompatible material so as to cause no undue detrimental effect on the eye into which the injection portion 14 is placed. The apparatus 10 may be made of a sterilizable material so that it can be conveniently reused, for example, many times. Examples of sterilizable materials from which apparatus 10 can be made include metals, such as stainless steel, titanium and the like.

The distally extending proximal and opening 18 of loading chamber 12 is configured to facilitate the folding of an IOL as it passes through this opening into the first lumen 20. In addition, the distal tapering of first lumen 20 assists in effecting and maintaining a controlled folding of an IOL passing therethrough.

Insertion apparatus 10 is sized and configured to fold an IOL carried by a forceps or similar grasping device passing through the distally extending proximal end opening 18 of loading chamber 12 into the first lumen 20. As the folded IOL passes from the loading chamber 12 into the injection portion 14, a rod 30, or forceps or similar pushing device may be employed to push the folded lens through the second lumen 22 and out the distal opening 26 of injection portion 14. The pushing device, for example, rod 30, can have any suitable cross-sectional configuration and tip shape. For example, the tip of rod 30 which is placed in contact with the folded IOL 40 may be blunt or have a concave configuration or other shape effective to facilitate passing the folded IOL through the second lumen 24 without damaging the IOL. Alternately, a forceps or similar device may be used to grasp the folded IOL in the second lumen and to pull (or carry) the folded IOL through the second lumen 22 and out of the distal opening 26 of injection portion 14. This forceps or similar device enters the second lumen 22 proximally. The forceps or similar device preferably releases the IOL after the IOL exits the second lumen.

Insertion apparatus 10 operates as follows. When it is desired to insert an IOL into an eye, an IOL 40, shown in the unfolded state in FIGS. 1 and 2, is grasped by a forceps 42. The IOL 40 includes a optic 44 and two filament type haptics 46 and 48. Insertion apparatus 10, which is typically packaged in sterile condition, is removed from its packaging and is ready for use. With IOL 40 in the grasp of forceps 42, the surgeon can make a final inspection of the IOL, for example, for structural damage. A lubricant, such as sodium hyaluronate and the like ophthalmically acceptable lubricants, may be applied to IOL 40 and/or the first lumen 20 and second lumen 24 to facilitate the passing of the IOL into and through the first and second lumens.

With particular reference to FIG. 2, IOL 40, grasped by forceps 42, is passed through distally extending proximal end opening 18 into the first lumen 20 of loading chamber 12. This passing causes the optic 44 of IOL 40 to fold upon itself so that it conveniently fits in the first lumen 20. The IOL 40, still in the grasp of forceps 42 is carried distally as far as possible. This results in the optic 44 of the IOL 40 being located at approximately the distal end 22 of loading chamber 12. At this point, the forceps 42 is withdrawn. Push rod 30 is then inserted to come in contact with the folded IOL 40. This push rod 30 is used to push folded IOL 40 through the second lumen 24 of injection portion 14. At this point, the IOL 40 and insertion apparatus 10 are ready to insert the IOL 40 into the eye.

Referring now to FIG. 4, the IOL 40 is to be placed in eye 50 into an area formally occupied by the natural lens of the eye. FIG. 4 shows the sclera 52 of the eye 50 having an incision through which the distal portion 54 of injection portion 14 may be inserted. Alternately, the incision can be made through both the cornea and sclera or only through the cornea. Distal portion 54 has a sufficiently small cross-section to pass into the eye 50 through a 3.2 mm incision in the sclera 52. The injection portion 14 is manipulated within eye 50 until it is positioned so that IOL 40 can be properly positioned in eye 50, that is in the anterior chamber, the posterior chamber, the capsular bag 56 or in the sulcus, after being released from insertion apparatus 10. Thus, the surgeon is able to controllably position injection portion 14 before releasing IOL 40. Once injection portion 14 is so positioned, the push rod 30 is moved distally so that IOL 40 passes through distal end opening 26 into eye 50. Insertion apparatus 10 is then withdrawn from the eye 50. If needed, the position of IOL 40 can be adjusted by a small, bent needle or similar tool inserted into the same incision.

Once the IOL 40 is properly placed in eye 50 and insertion apparatus 10 is withdrawn from the eye, the incision in the sclera 52 may be mended, for example, using conventional techniques. After use, insertion apparatus 10 is preferably disposed of.

Alternately, with particular reference to FIG. 6 and with the IOL 40 located in a folded position in the second lumen 24, the apparatus 10 is removably secured to one end 58 of a hand tool 60 so that the surgeon, holding the handle or housing 62 of the hand tool, can conveniently manipulate apparatus 10, for example, in eye 50. Also, other types of insertion systems may be used in conjunction with apparatus 10. For example, apparatus 10 may be used as a cartridge in the barrel of a lens inserter. In this embodiment, the injection portion 14 may or may not be inserted in the eye during lens insertion. However, the principles set forth herein apply whether the injection portion 14 is inserted in the eye or passes the folded IOL 40 to another lumen from which the IOL eventually is passed into the eye.

The present IOL insertion apparatus are straight-forward in construction and use. Such apparatus are proximally loaded with an IOL to be inserted into an eye to avoid undue stress on the lens and/or on the insertion apparatus itself. The configuration of the apparatus facilitates the folding of the IOL for insertion. At the same time, the loading chamber is structured and has sufficient size so that a forceps or similar grasping device can be used to pass the IOL into and at least partially through the lumen defined by the loading chamber. Moreover, the preferred one piece construction of the present apparatus facilitates its easy and effective use.

While this invention has been described with respect to various specific examples and embodiments, it is to be understood that the invention is not limited thereto and that it can be variously practiced within the scope of the following claims.

What is claimed is:

1. An apparatus for insertion of an intraocular lens into a small incision in an eye, comprising:

a loading chamber having a proximal end, a distal end and a sidewall including a distally extending through opening which terminates proximally of said distal end, said loading chamber defining a first lumen having a cross-section which gradually decreases at a substantially constant rate from the termination of said through opening to said distal end and being adapted to receive an intraocular lens in an unfolded state and to fold said intraocular lens and maintain said intraocular lens folded as said intraocular lens is placed in said first lumen; and an injection portion joined to said loading chamber, defining a second lumen having a length aligned with and directly adjacent said first lumen, said second lumen having a cross-section which gradually decreases at a substantially constant rate distally throughout said length and being adapted to receive said folded intraocular lens from said first lumen , said second lumen having a distal end opening for passing said folded intraocular lens from said second lumen directly into an eye.

2. The apparatus of claim 1 wherein said proximal end of said loading chamber is open and said distally extending through opening is formed by a distally extending through notch in said sidewall which extends to said proximal end of said loading chamber.

3. The apparatus of claim 2 wherein said distally extending through notch is configured to facilitate the folding of said intraocular lens as said intraocular lens is placed in said first lumen.

4. The apparatus of claim 1 wherein said second lumen has an elliptical cross-section through said length.

5. The apparatus of claim 1 wherein said first lumen has a elliptical cross-section at said distal end.

6. A method for inserting an intraocular lens into a small incision in an eye, comprising:

placing an intraocular lens in an apparatus as defined in claim 1, said injection portion of said apparatus having a distal end portion;

placing said distal end portion of said injection portion in close relation to an eye; and causing said intraocular lens to pass out of said distal end opening of said injection portion and into the eye.

7. The method of claim 6 wherein said causing step comprises at least one of pushing and pulling said intraocular lens out of said distal end opening.

8. The method of claim 6 wherein said intraocular lens in an unfolded state is grasped by a forceps and is placed in said first lumen of said loading chamber.

9. An apparatus for insertion of an intraocular lens into a small incision in an eye, comprising:

a loading chamber defining a first lumen and having a distal end and an open proximal end which includes a distally extending through notch in said loading chamber terminating proximally of said distal end, said first lumen having a cross-section which gradually decreases at a substantially constant rate from said termination of said through notch to said distal end, said loading chamber being adapted to receive an intraocular lens at said open proximal end and to fold said intraocular lens and maintain said intraocular lens folded as said intraocular lens is passed into and through said first lumen; and an injection portion defining a second lumen contiguous with said first lumen, having a length and a cross-section which gradually decreases at a substantially constant rate distally throughout said length and being adapted to receive said folded intraocular lens from said first lumen, said injection portion having a distal end opening for pushing said folded intraocular lens from said second lumen directly into an eye, said loading chamber and said injection portion being a unitary structure terminating proximally at said open proximal end.

10. The apparatus of claim 9 wherein said injection portion is biocompatible.

11. The apparatus of claim 9 wherein said injection portion has a distal end sized to pass into a 3.2 mm or smaller incision in an eye.

12. The apparatus of claim 9 wherein said open proximal end defines an opening sized and configured to facilitate folding an intraocular lens passing through said open proximal end into said first lumen.

13. The apparatus of claim 12 wherein said opening has a non-circular configuration.

14. The apparatus of claim 9 wherein said distally extending through notch is configured to facilitate the folding of said intraocular lens passing through said open proximal end into said first lumen.

15. The apparatus of claim 6 wherein said injection portion includes a distal end portion adapted to be placed in the eye when said intraocular lens in said injection portion is inserted into the eye.

16. A method for inserting an intraocular lens into a small incision in an eye, comprising:

placing an intraocular lens in an apparatus as defined in claim 6, said injection portion of said apparatus having a distal end portion;

placing said distal end portion of said injection portion in close relation to an eye; and causing said intraocular lens to pass out of said distal end opening of said injection portion and into the eye.

17. An apparatus for insertion of an intraocular lens into a small incision in an eye, comprising:

a loading chamber defining a first lumen having an open proximal end, a distal end and a sidewall with a distally extending through opening therein which terminates proximally of said distal end, said open proximal end and said distally extending through opening together defining a proximal opening, said first lumen having a cross-section which gradually decreases at a substantially constant rate from the termination of said distally extending through opening to said distal end, said loading chamber being adapted to receive an intraocular lens in an unfolded state at said open proximal end and to fold said intraocular lens and maintain said intraocular lens folded as said intraocular lens is passed into and through said first lumen, said proximal opening is non-circular and is sized and configured to facilitate folding said intraocular lens passing through said proximal opening; and an injection portion joined to said loading chamber, defining a second lumen having a length aligned with and directly adjacent said first lumen, said second lumen having a cross-section which gradually decreases at a substantially constant rate distally throughout said length and being adapted to receive an intraocular lens in a folded state from said first lumen and having a distal end opening through which said folded intraocular lens from said second lumen passes to be directly inserted into an eye.

18. The apparatus of claim 17 wherein said injection portion includes a distal end portion adapted to be placed in the eye when said intraocular lens in said injection portion is inserted into the eye.

19. A method for inserting an intraocular lens into a small incision in an eye, comprising:

placing an intraocular lens in an apparatus as defined in claim 17, said injection portion of said apparatus having a distal end portion;

placing said distal end portion of said injection portion in close relation to an eye; and causing said intraocular lens to pass out of said distal end opening of said injection portion and into the eye.

20. An inserter for folding and inserting a flexible intraocular lens through a small incision into the eye comprising:

a loading chamber having a generally tubular body providing a first lumen with a proximal end and a distal end adapted to receive an unfolded intraocular lens at said proximal end;

said loading chamber having a longitudinal axis and said first lumen having a cross-sectional area at any point on said longitudinal axis measured perpendicular to such axis, said cross-sectional area gradually decreasing from said proximal end to said distal end to effectuate a folding of the intraocular lens as the intraocular lens is passed therethrough;

the body of said loading chamber having a distally extending opening at said proximal end to facilitate the folding of the intraocular lens as the intraocular lens is loaded in said proximal end, said distally extending opening terminating proximally of said distal end, said cross-sectional area gradually decreasing at a substantially constant rate from the termination of the distally extending opening to said distal end; and an injector portion providing a second lumen contiguous with said first lumen, said second lumen having a length and a cross-sectional area measured perpendicular to said longitudinal axis which gradually decreases at a substantially constant rate distally throughout said length for passing said folded intraocular lens from said distal end of said first lumen through said second lumen directly into the eye.

21. The inserter of claim 20 wherein said distally extending opening is a non-circular proximal opening which terminates proximally of said distal end.

* * * * *